(12) United States Patent
Koshti et al.

(10) Patent No.: US 10,675,232 B2
(45) Date of Patent: Jun. 9, 2020

(54) COLD PROCESSABLE NON-TOXIC PRESERVATIVE COMPOSITION FOR HOME AND PERSONAL CARE PRODUCTS

(71) Applicant: GALAXY SURFACTANTS LTD., Navi Mumbai (IN)

(72) Inventors: Nirmal Koshti, Piscataway, NJ (US); Arpit Wankhade, Amravati (IN); Bhagyesh Jagannath Sawant, Kalyan (IN); Devyani Mali, Morivali (IN); Shraddha Ratnaparkhe, Thane (IN)

(73) Assignee: GALAXY SURACTANTS LTD., Navi Mumbai (IN)

( * ) Notice: Subject to any disclaimer, the term of this patent is extended or adjusted under 35 U.S.C. 154(b) by 0 days.

(21) Appl. No.: 15/653,297

(22) Filed: Jul. 18, 2017

(65) Prior Publication Data

US 2018/0193243 A1    Jul. 12, 2018

(30) Foreign Application Priority Data

Jan. 12, 2017    (IN) .............................. 201721001340

(51) Int. Cl.

| | |
|---|---|
| *A61K 8/44* | (2006.01) |
| *A61K 8/49* | (2006.01) |
| *A61K 8/02* | (2006.01) |
| *C07C 63/06* | (2006.01) |
| *C11D 3/20* | (2006.01) |
| *A61Q 17/00* | (2006.01) |
| *A61Q 19/10* | (2006.01) |
| *C11D 3/48* | (2006.01) |
| *C11D 1/37* | (2006.01) |
| *A61K 8/368* | (2006.01) |
| *C07C 233/49* | (2006.01) |
| *C07D 309/30* | (2006.01) |
| *C11D 1/10* | (2006.01) |
| *A61Q 5/02* | (2006.01) |

(52) U.S. Cl.
CPC .............. *A61K 8/445* (2013.01); *A61K 8/022* (2013.01); *A61K 8/368* (2013.01); *A61K 8/44* (2013.01); *A61K 8/498* (2013.01); *A61Q 17/005* (2013.01); *A61Q 19/10* (2013.01); *C07C 63/06* (2013.01); *C11D 1/37* (2013.01); *C11D 3/2079* (2013.01); *C11D 3/2096* (2013.01); *C11D 3/48* (2013.01); *A61Q 5/02* (2013.01); *C07C 233/49* (2013.01); *C07D 309/30* (2013.01); *C11D 1/10* (2013.01)

(58) Field of Classification Search
CPC .................................. C07C 63/06; C11D 3/48
See application file for complete search history.

(56) References Cited

U.S. PATENT DOCUMENTS

| 10,015,963 B2 * | 7/2018 | Koshti ..................... A61K 8/34 |
|---|---|---|
| 2001/0002257 A1 | 5/2001 | Stolz |
| 2007/0196315 A1 | 8/2007 | McDonald et al. |
| 2013/0101530 A1 | 4/2013 | Koshti et al. |
| 2013/0336903 A1 * | 12/2013 | Fernandez Prieto .... A61K 8/42 424/59 |
| 2014/0309302 A1 | 10/2014 | Koshti et al. |

FOREIGN PATENT DOCUMENTS

| FR | 2771632 | 4/1999 |
|---|---|---|
| JP | 4909241 A | 9/1974 |
| WO | 92/20647 | 11/1992 |
| WO | 92/21318 | 12/1992 |
| WO | 94/26694 | 11/1994 |
| WO | 94/27561 | 12/1994 |

OTHER PUBLICATIONS

Badreshia, et al., "Iodopropynyl Butylcarbamate", Am. J. of Contact Derm., vol. 13, No. 2 Jun. 2002: pp. 77-79.
Curry, et al., "Benzyl Alcohol Allergy: Importance of Patch Testing with Personal Products", Dermatitis, vol. 16, No. 4 Dec. 2005: pp. 203-208.
Degroot, et al., "Isothiazolinone Preservative: Cause of a Continuing Epidemic of Cosmetic Dermatitis", The Lancet, Feb. 11, 1989, pp. 314-316.
Du, et al., "In Vitro Neurotoxicity of Methylisothiazolinone, a Commonly Used Industrial and Household Biocide, Proceeds via a Zinc and Extracellular Signal-Regulated Kinase Mitogen-Activated Protein Kinase-Dependent Pathway", The J. of Neuroscience, Sep. 1, 2002, 22(17): 7408-7416.
Jacob, et al., "Allergen Focus, Skin and Aging, 32-35, May 2005", https://www.the-dermatologist.com/article/1791.
Kang, et al., "Decreased Sperm Number And Motile Activity on the F1 Offspring Maternally Exposed to Butyl-p-Hydroxybenzoic Acid (Butyl Paraben)", J. Vet Med. Sci. 64(3): 227-23, 2002.
Kumar, et al., "Alteration of testicular steroidogenesis and histopathology of reproductive system in male rates treated with triclosan", Reproductive Toxicology 27 (2009) 177-185.
Pedersen, et al., "The Preservatives Ethyl-, Propyl- and Butylparaben are Oestrogenic in an in vivo Fish Assay", Pharm. & Toxic. 2000, 86, 110-113.
Prosperio, et al., "Nonpreservative substances able to inhibit microbial growth in cosmetics", Cosmetics & Toiletries, Edizione Italiana (1996), 17(3), pp. 16-19.
Schmuck, et al., "2-Phenoxyethanol: a neurotoxicant?", Arch. Toxicol. (2000) 74: 281-283.
Zorrilla, et al., "The Effects of Triclosan on Puberty and Thyroid Hormones in Male Wistar Rats", Toxicological Sciences 107(1): 56-64 (2009).

* cited by examiner

*Primary Examiner* — Kyle A Purdy

(74) *Attorney, Agent, or Firm* — Kramer Amado, P.C.

(57) ABSTRACT

Disclosed herein is a cold-processable antimicrobial composition in non-dusting solid form, free from toxic antimicrobial comprising, a) N-caployl glycine (Formula I), b) N-undecylenoyl glycine (Formula II), c) benzoic acid (Formula III) and d) sodium dehydroacetate (Formula IV) for use in personal care and home care products. The invention further discloses a process for preparation of the antimicrobial composition and ease of its incorporation in various personal and home products.

9 Claims, 1 Drawing Sheet

COLD PROCESSABLE NON-TOXIC PRESERVATIVE COMPOSITION FOR HOME AND PERSONAL CARE PRODUCTS

FIELD OF INVENTION

The present invention relates to a broad spectrum cold processable preservative composition in the form of non-dusting composite blend based on non-toxic antimicrobials for home and personal care products. The preservative composition is free from halogenated chemicals (Methylchloroisothiazolinone, Iodopropynyl butyl carbamate, Triclosan, Chlorphenesin, Bronopol), phenolic molecules (parabens), formaldehyde releasers (DMDM Hydantoin and other urea derivatives) and alcoholic/glycolic molecules (phenoxy ethanol, benzyl alcohol). This preservative composition is not only easy-to-use but also eco-friendly.

BACKGROUND OF THE INVENTION

Preserving personal care products from microbial degradation is quite challenging. Most topical cosmetics and dermatological products in the form of creams, lotions, gels, shampoos, body-washes and face-washes contain significant amount of water. This provides a very hospitable environment for the microbial growth. In addition to water, other cosmetic ingredients can also be a good source of nutrients to microbes. Another pertinent point to be reckoned here is that the shelf-life of the personal care products and the period after opening the container by the consumer is quite long compared to pharmaceutical products or food products. Unlike pharmaceutical products, cosmetics products are neither sterilized nor packed in hermetic conditions. Thus, the requirement for preservation of the personal care products is, indeed, quite challenging. This is further compounded by the limited choice of antimicrobials since the available approved antimicrobials are very few and those which have good antimicrobial activity are quite toxic. Consumers want products meant for topical applications to be free from toxic antimicrobials that are used as preservatives. Very effective antimicrobials that are used currently, are implicated in serious toxicity issues to human as well as to environment. For example, parabens are implicated in disrupting endocrine system, ultimately linked to breast cancer [(Pharmacology & Toxicology (Vol. 86(3), pp 110-13, March 2000, Toxicology and Applied Pharmacology (Vol. 153(1), pp. 12-19 (November 1998), *Journal of Veterinary Medical Science* (Vol. 64(3), pp. 227-35 (March 2002, *Journal of Applied Toxicology*, 24 (3): 167-176, (2004)]. Formaldehyde is classified as Category 3 CMR (carcinogenic, mutagenic and reproductive toxic) and hence all formaldehyde releasers are under the cloud. This class includes the work-horse preservatives such as DMDM hydantoin, diazolidinyl urea, imidazolidinyl urea and Quaternary 15.

Another class of very effective antimicrobials is 'isothiazolinones'. Methyl and Chloromethyl isothiazolinones have been used in personal care but they are reported to be neurotoxic and skin sensitizers (Journal of Neuroscience 22 (17): 7408-7416. The Lancet, Volume 333, Issue 8633, Pages 314-316 (1989). Chloromethyl isothiazolinone (generally abbreviated as CIT) is far more toxic and most of the leading personal care products manufacturers have stopped using it.

Halogenated antimicrobials have their own share of toxicity issues. For example, Triclosan, once a popular antimicrobial for hand sanitizers, is being phased out due to its toxicity. It has been implicated in eco-toxicity issues (algae, dolphins). It is reported to be an endocrine disruptor (thyroid function) and is reported to impair cardiac and skeletal muscles. There seems to be special concern for children who are at higher risk of allergies and the immune systems (Toxicological Sciences, 2009, 107 (1): 56-64, Reproductive Toxicology, April 2009, 27(2): 177-185). Companies such as Johnson and Johnson, P & G and Reckitt Benckiser have either removed it or announced the plan of complete phasing it out from their products in a given short time frame. Triclosan's ecotoxicity is such a big concern that state of Minnesota in the USA has completely banned its use. Iodopropynyl butyl carbamate, another halogenated antimicrobial, is a contact allergen (American Journal of contact dermatitis 13(2), 77-79 (2002). The presence of iodine in the molecular structure gets it implicated in Goiter and malfunctioning thyroid gland. It is not allowed in Japan and in European Union (EU) and generally, elsewhere, it is allowed only up to 0.02% in leave-on products. Similarly, EU permits usage of methyl dibromo glutaronitrile only up to 0.1% and that too in only rinse-off products. Another brominated molecule is Bronopol, very widely used once upon a time, is banned today in countries like Canada for its application in cosmetics. It is involved in allergic reactions as well as generation of N-nitroso amines that are known to be carcinogenic. The quaternary ammonium compounds (examples are cetyl pyridinium chloride, benzethonium chloride, benzalkonium chloride) exhibit good antimicrobial activity but their utility in personal care industry is limited due to specific incompatibilities with other cosmetic ingredients, particularly with the ingredients of strong anionic nature.

To avoid the above mentioned toxic antimicrobials, the industry did come up with alternatives that are largely based on organic acids such as sorbic acid, benzoic acid, dehydroacetic acid, and alcohols such as phenoxyethanol, benzyl alcohol and other glycols or glycol ethers that are not listed as preservatives by Cosmetics Directive Annex VI (propylene glycol, 2-ethyl hexyl glycerin, caprylyl glycol, 1,2-hexane diol).

The survey of such recent products shows that the most common ingredient in these preservative blends is phenoxyethanol as shown in Table I below.

TABLE I

| Name | Company Name | INCI Name |
| --- | --- | --- |
| McKinley CG4 | McKinley Resources Incorporated | Phenoxyethanol, Caprylyl Glycol |
| euxyl ® K 940 | Schülke Inc. | Phenoxyethanol, Benzyl Alcohol, Ethylhexylglycerin |
| euxyl ® PE 9010 | Schülke Inc. | Phenoxyethanol, Ethylhexylglycerin |
| CaribNat K | Caribbean Natural Products Inc. | Phenoxyethanol, Potassium Sorbate |

TABLE I-continued

| Name | Company Name | INCI Name |
| --- | --- | --- |
| Sharon Biomix Clear Liquid | Sharon Labs | Phenoxyethanol, Citrus Aurantium Amara (Bitter Orange) Fruit Extract, Citrus Reticulata (Tangerine) Fruit Extract, Citrus Aurantium Sinensis Peel Extract |
| Sharomix HPD | Sharon Labs | Phenoxyethanol, 1,2-Hexanediol, Dehydroacetic Acid |
| Saliguard ® BDP | Salicylates and Chemicals | Phenoxyethanol, Benzoic Acid, Dehydroacetic Acid |
| Verstatil ® BP | Dr. Straetmans | Phenoxyethanol, Benzoic Acid |
| Solbrol ® PEH | Lanxess Distribution | Phenoxyethanol, Ethylhexylglycerin |
| SymOcide ® PT | Symrise | Phenoxyethanol, Tropolone |
| Sharomix EG14 | Sharon Labs | Phenoxyethanol, Ethylhexylglycerin |
| Verstatil ® MPC | Dr. Straetmans | Phenoxyethanol, Methylpropanediol, Caprylyl Glycol |
| Pentaglycan PF | DSM Nutritional Products, LLC | Phenoxyethanol, Glycosaminoglycans, Benzoic Acid, Dehydroacetic Acid, Sodium Hyaluronate |
| Nipaguard ® SCV | Clariant - Personal Care | Phenoxyethanol, Sorbitan Caprylate, Phenoxyethanol, Benzyl Alcohol, Benzoic Acid |
| Saliguard ® PCG | Salicylates and Chemicals | Phenoxyethanol, Caprylyl Glycol, Phenoxyethanol, Propylene Glycol |
| Saliguard ® PG | Salicylates and Chemicals | Phenoxyethanol, Caprylyl Glycol |
| Saliguard ® UCP | Salicylates and Chemicals | Phenoxyethanol, Undecylenic acid, Caprylyl Glycol |
| Rokonsal ™ BSP | Ashland Inc. | Phenoxyethanol, Propylene Glycol, Benzoic Acid, Sorbic Acid |
| Optiphen ™ 200 | Ashland Inc. | Phenoxyethanol, Caprylyl Glycol |
| Optiphen ™ ND | Ashland Inc. | Phenoxyethanol, Benzoic Acid, Dehydroacetic Acid |
| Optiphen ™ Plus | Ashland Inc. | Phenoxyethanol, Caprylyl Glycol, Sorbic Acid |
| Optiphen ™ 300 | Ashland Inc. | Phenoxyethanol, Caprylyl Glycol |
| Sharomix 710 | Sharon Labs | Phenoxyethanol, Benzoic Acid, Sorbic Acid, Dehydroacetic Acid Caprylyl Glycol, Phenoxyethanol |
| Sharomix 704 | Sharon Labs | Phenoxyethanol, Benzoic Acid, Sorbic Acid, Dehydroacetic Acid |
| Sharomix 702 | Sharon Labs | Phenoxyethanol, Dehydroacetic Acid, Benzoic Acid |
| Optiphen ™ BSP | Ashland Inc. | Phenoxyethanol, Benzoic Acid, Sorbic Acid |
| Nipaguard ™ POB | Clariant - Personal Care | Phenoxyethanol, Benzoic Acid, Piroctone Olamine |
| Nipaguard ™ PO 5 | Clariant - Personal Care | Phenoxyethanol, Piroctone Olamine |
| Unigard OA-94 | Givaudan Active Beauty | Phenoxyethanol, Benzoic Acid, Dehydroacetic Acid |
| Lincocide ™ PHOE - BS | Lincoln Fine Ingredients | Phenoxyethanol, Propylene Glycol, Benzoic Acid, Sorbic Acid |
| SymOcide ® PS | Symrise | Phenoxyethanol, Decylene Glycol, 1,2-Hexanediol |
| Verstatil ® PC | Dr. Straetmans | Phenoxyethanol, Caprylyl Glycol |
| Rokonsal ™ ND | Ashland Inc. | Phenoxyethanol, Benzoic Acid, Dehydroacetic Acid |
| SymOcide ® PH | Symrise | Phenoxyethanol, Caprylyl Glycol |
| Blueguard C5 | Blue Sun International | Phenoxyethanol, Caprylyl Glycol, Potassium Sorbate, Hexylene Glycol |
| Lexgard ® HPO | INOLEX | Phenoxyethanol, Caprylyl Glycol, Hexylene Glycol |
| Phenostat ™ | INOLEX | Phenoxyethanol, Caprylhydroxamic Acid, Methylpropanediol |
| SharoSENSE ™ 250 | Sharon Labs | Phenoxyethanol, Thymol, Linalool |

These compositions listed in Table I avoid toxic antimicrobials like halogenated, phenolic molecules or isothiazolinones and rely heavily on phenoxyethanol wherein phenoxyethanol is combined with 2-ethyl hexyl glycerin, caprylyl glycol, benzoic acid and dehydroacetic acid, and fruit extracts.

In addition to above commercial products some recent patent applications also disclose preservative combinations wherein Phenoxyethanol is combined with molecules like undecylenoyl monoethanolamide, undecylenoyl glycine or capryloyl glycine (US20140309302 A1 and US20130101530 A1).

2-Phenoxyethanol is indeed a work-horse antimicrobial for personal care industry. In the recent past some doubts have been cast and the regulatory committee from EU did clear it after a thorough review. Despite the clearance from the Scientific Community of Consumer Safety of EU the concern remains because of inadequate data on toxicity.

Maximum concentration that has been generally allowed is up to 1.0% (Cosmetics Directive Annex VI), however, for last few years France has been raising their concern for its use level for children's products, particularly nappy area products. In South Korea it is not allowed in products like wet wipes particularly meant for babies.

In September 2012, the Commission received a risk assessment submitted by the French Agency ANSM (Agence nationale de sécurité des médicaments et des produits de santé) which rose concerns about the use of Phenoxyethanol as preservatives in cosmetic products.

The ANSM report (Evaluation du risque lié à l'utilisation du phénoxyéthanol dans les produits cosmétiques) concludes that the maximum authorized concentration (currently of 1%) of Phenoxyethanol for use as a preservative should be lowered to 0.4% in cosmetic products for children who are less than three years old.

On October 6th 2016 Scientific Community of Consumer Safety (SCCS) finally declared it to be safe up to 1.0% level for cosmetics. However, the concern remains with the manufacturers of personal care products because of Phenoxyethanol's belonging to the dangerous glycol ether family (methyl cellosolve or ethyl cellosolve, phenoxy ethanol is phenyl cellosolve (scheme 1). The scheme 1 as depicted below explains the structural similarity between glycol ethers (methyl, ethyl cellosolves) and phenoxy ethanol.

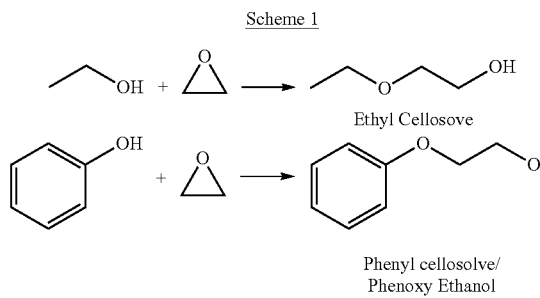

Phenoxyethanol is also reported to depress the central nervous system (Schmuck G, Steffens W, Bomhard E (July 2000). "2-Phenoxyethanol: a neurotoxicant?" *Archives of Toxicology*. 74 (4-5): 281-7) and it may cause vomiting and diarrhea, which can lead to dehydration in infants. US FDA warned about Mommy's Bliss nipple cream where phenoxyethanol is used as preservative along with chlorphenesin.

In view of phenoxyethanol's structural similarity to glycol ether family (Scheme 1) and its reported neurotoxicity, manufacturers of personal care products and particularly, the baby care products, are wary of using it as preservative and are looking for safe alternatives.

For example, Colgate's baby care brand Tom's of Maine, avoids use of phenoxyethanol in moisturizing lotion for babies.

There has been an attempt in the commercial world to avoid all toxic antimicrobials including phenoxyethanol. Examples of such products are Sharon Mix 705, Sharon Mix 705plus, Sharon Mix 706 and Sharon Mix 706plus from Sharon Laboratories, Israel. These products are based on benzyl alcohol and organic acids like benzoic acid, sorbic acid and dehydroacetic acid.

Though these commercial compositions from Sharon Labs avoid use of phenoxyethanol, the choice of benzyl alcohol is not the most ideal one. Benzyl alcohol has comparable antimicrobial properties to phenoxyethanol. In fact, benzyl alcohol has slightly better antimicrobial activity than phenoxy ethanol (Minimum growth inhibition concentrations). The simple reason for benzyl alcohol's lesser usage than phenoxyethanol is benzyl alcohol's strong benzaldehyde like odor. This strong aromatic odor puts limitation on the usage since it is difficult to mask the characteristic odor of benzyl alcohol. Also, serious allergic contact dermatitis reactions have been reported with products containing benzyl alcohol (E. J. Curry and E. M. Warshaw, Dermatitis, 2005; 16 (4):203-208). Delayed contact dermatitis reactions as well as immediate, urticarial and systemic reactions have been reported to occur with its use in these various formulations (Sharon Jacob and Giuseppe Militello, Allergen Focus, Skin and Aging, 32-35, May 2005). Benzyl alcohol is a rare allergen but the fact is that it is an allergen.

So in view of the limitations, restrictions and concerns cited above for the majority of antimicrobials, it is important to develop a safe, broad spectrum, organoleptically acceptable antimicrobial composition, avoiding all the toxic and controversial substances for personal care and for home care industry.

OBJECT OF INVENTION

Therefore, it is an objective of the present invention to provide a broad spectrum (effective against bacteria, yeast and mold) preservative composition for personal care and home care products avoiding all reported toxic antimicrobials.

It is another objective of the present invention to develop an easy-to-use and ecofriendly antimicrobial composition for personal care and home care products.

SUMMARY OF INVENTION

In the first aspect, the present invention is directed to a stable, homogeneous, cold processable preservative composition in the form of non-dusting composite blend, which comprises;

a) N-capryloyl glycine (Formula I), b) N-undecylenoyl glycine (Formula II), c) benzoic acid (Formula III) and d) sodium dehydroacetate ((Formula IV) wherein, the ratio of above four components to each other is 1:1:1:1 by weight.

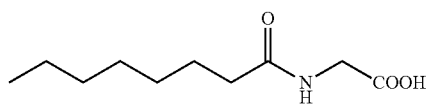

Formula I

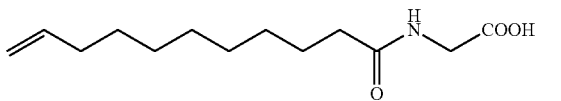

Formula II

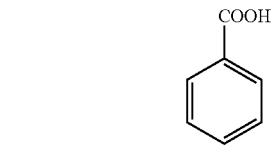

Formula III

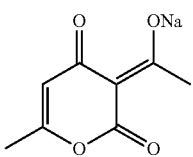

Formula IV

In another aspect, the present invention is directed to personal care and home care compositions containing the preservative blend of the present invention.

The above described features, benefits and advantages of the present disclosures will be appreciated and understood by those skilled in the art from the following detailed description and the claims.

DETAILED DESCRIPTION OF INVENTION

Figure 1:
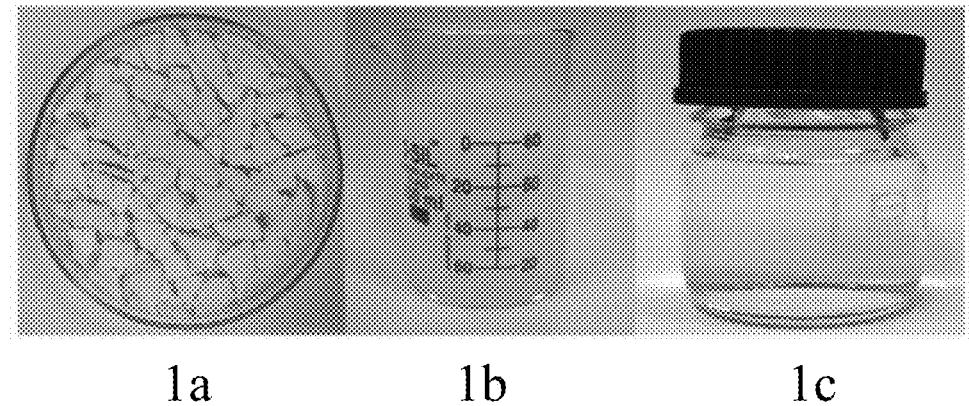
FIG. 1 shows 1a) typical flake form of the composition 1b) aqueous fine dispersion at 1% at room temperature and 1c) depicts clear solution of this dispersed antimicrobials at room temperature in the presence of 8 to 10% surfactant mix, typically anionic or amphoteric surfactants.

The present invention relates to a broad spectrum, cold processable antimicrobial preservative composition in the form of non-dusting composite blend for use in personal care and home care products.

The term "blend", as used in the specification refers to an admixture of 1) N-capryloyl glycine (CG), 2) N-undecylenoyl glycine (UG), 3) benzoic acid (BA) and 4) sodium dehydroacetate (SDA).

The phrase "composite blend" as used in the specification refers to the composition obtained as per the process described in example 2.

As described in the background, most of the highly efficient preservatives of yesteryear are seriously mired into toxicity issues and are being consciously phased out by the personal care industry. These include parabens, isothiazolinones, formaldehyde releasers, chlorinated molecules, brominated molecules, iodinated substances, phenolic molecules and quaternary ammonium type molecules. Some manufacturers of antimicrobial preservatives (Table I in the 'background of the invention' section) came up with idea of blending safe antimicrobials like organic acids with phenoxyethanol. However, in view of certain reservations about phenoxyethanol for the want of adequate safety data and its structural similarity with toxic glycol ethers, a need is felt by the present inventors to create antimicrobial compositions without phenoxyethanol. Phenoxyethanol is a CNS depressant and the reasons for requesting reassessment and the restrictions imposed are explained in the 'background' section. Hence there remains a definite need for antimicrobial preservative compositions for personal and home care products without phenoxyethanol. This need has been partly addressed by replacing phenoxyethanol by benzyl alcohol. Only a couple of compositions are in the market wherein phenoxyethanol has been replaced by benzyl alcohol. The compositions have been created using benzyl alcohol along with other organic acids. Benzyl alcohol has strong benzaldehyde like odor and that restricts its usage in personal care formulations. Even today, phenoxyethanol is more widely used than benzyl alcohol. (October 2016, Mintel, where Ingredient Search matches one or more of [Phenoxyethanol, Benzyl Alcohol] as the Ingredients; Mintel Group Ltd is a privately owned, London-based market research firm.) Thus, it can be seen by referring to Table 1 in 'background' section that benzyl alcohol is not a good substitute for phenoxyethanol since several antimicrobial blends in the market today are based on phenoxyethanol.

Accordingly, in an embodiment, the present patent invention provides efficacious preservative composition in the form of non-dusting composite blend which comprises well-known and well accepted personal care ingredients. The composition of the present invention is based on four organic acids that address the safety and efficacy problems adequately by providing the coverage against both bacteria and fungi. The preservative composition of the present invention comprises a combination of 1) N-capryloyl glycine (CG), 2) N-undecylenoyl glycine (UG), 3) benzoic acid (BA) and 4) sodium dehydroacetate (SDA), wherein, the ratio of the N-capryloyl glycine:N-undecylenoyl glycine:benzoic acid:sodium dehydroacetate may range from 1:1:1:1.

Details of the Components of the Present Composition

Lipoaminoacids (N-acylated amino acids) are described in WO 92/20647, WO 92/21318, WO 94/26694, and WO 94/27561 as amphiphilic biological vectors that are advantageous as regulators of skin physiology and are shown to be suitable for many different applications in cosmetics.

N-Capryloyl Glycine:

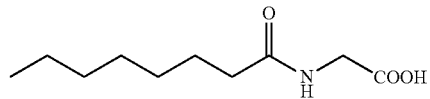

Formula I

N-capryloyl glycine, also known as N-octanoyl glycine (CAS No. 14246-53-8) is also well-known for its action against naturally occurring micro-flora that is resident of skin. The use of this antimicrobial was suggested way back in 1996, as a non-preservative substance that can inhibit microbial growth in cosmetics (Proserpio, Gianni; Cattaneo, Roberta C & T, Edizione Italia 17(3), 11-13, 16-19, (1996). It offers derma-protection for the restoration of the skin's acid mantle and purification through dandruff reduction by the inhibition of *Pityrosporum ovale*. It is commercially available under the trade name Lipacide C8G from SEPPIC.

N-Undecylenoyl Glycine:

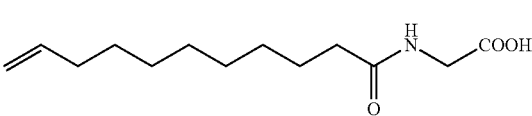

Formula II

Almost four decades ago N-undecylenoyl amino acids were reported for the treatment of skin disorders (JP 49093521, 1974). One of them is N-Undecylenoyl glycine (CAS No 54301-26-7) is a well-known derma-purifier with very pronounced anti-acne and anti-dandruff activity. It is commercially available under the trade name Lipacide UG from SEPPIC, France. SEPPIC reported (FR 2771632 A1) cosmetic compositions containing undecylenoyl glycine along with capryloyl glycine in 1999. Corinne Stolz, (US 20010002257A1) disclosed compositions comprising undecynoyl glycine and capryloyl glycine along with tannin rich plant extracts that showed activity against skin flora. Interestingly, in 2004, use of combination of Wasabi extract along with undecylenoyl glycine and capryloyl glycine as co-preservatives for protection of personal care preparations was reported by D. Misner (U.S. 2004/096528 A1). Kabara et al. (U.S. Pat 2007/0196315 A1) reported preserved botanical extracts with capryloyl glycine, undecylenoyl glycine, glyceryl monolaurate and pentylene glycol.

Benzoic Acid:

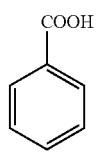

Formula III

Maximum allowed concentration of benzoic acid (CAS No 65-85-0) (Cosmetics Directive Annex VI) is 2.5% in 'rinse-off' and 0.5% in 'leave-on' product. For oral products the permissible concentration is 1.7%. It is well-known antimicrobial with specific action against fungi. Hence it is widely used in food products as preservative.

Sodium Dehydroacetate:

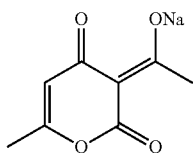

Formula IV

Maximum authorized concentration of sodium dehydroacetate (CAS number 520-45-6) according to Cosmetics Directive Annex VI is 0.6%. In the USA and EU the maximum allowed concentration is 0.6% whereas in Japan is it is 0.5% in the final personal care products. It is a good fungicide and mild bactericide.

In another preferred embodiment, the invention provides process for preparation of preservative composition in the form of non-dusting composite blend which comprises;
a) Melting a blend of N-capryloyl glycine and N-undecylenoyl glycine in 1:1 ratio by weight to obtain molten mass;
b) Adding benzoic acid and sodium dehydroacetate in 1:1 ratio by weight to the molten mass under stirring at about 75° C. till the reaction mass becomes clear; and
c) Cooling the blend to obtain non-dusting solid form of preservative composition.

The cooled composite blend can be obtained in the non-dusting solid forms such as cubes, flakes (example 2), granules etc. by pouring the same in shaped molds or by spreading it on a metal or glass surface uniformly or by spray drying to obtain in granules etc.

According to this process a blend of N-Capryloyl glycine and N-undecylenoyl glycine (1:1 by weight) is synthesized in one pot as described in Example No 1. The dry powder of mixture of N-capryloyl glycine and N-undecylenoyl glycine in (1:1 ratio by weight) is then melted (90° C.) under nitrogen atmosphere and to this stirred molten mass, benzoic acid and sodium dehydroacetate (1:1 ratio by weight) are added and stirring is continued at 75° C. till the reaction mass becomes clear. This molten composite blend is then flaked by spreading it on a metal or glass surface uniformly to get a very thin (2 to 4 mm) off-white flakes upon cooling and scraping (Example 2). The melting point range of these flakes is from 55 to 65° C. and acid value ranges from 235 to 240.

The preservative composite blend in flake form thus obtained is completely free from dust explosion hazard and other health hazard to human while handling the material. The thin flake form avoids handling of these solid organic acids in powder form and the dust explosion hazard. The minimum ignition energy of 1:1 mixture of N-capryloyl glycine and N-undecylenoyl glycine is as low as 55 mJ. Using this process (Example 1 & 2) it is very apparent to anyone with reasonable knowledge in microbiology that ratios of four components can be varied a little and still can get the effective broad spectrum of antimicrobial activity, for example, ratio of N-capryloyl glycine:N-undecylenoyl glycine:benzoic acid:sodium dehydroacetate can be 1:1:1.25:0.75 or it can be 1.25:0.75:1.0:1.0 by weight. Many such combinations can be worked out with overall broad range of antimicrobial activity. However, excellent cold-processability results from the composition comprising N-capryloyl glycine:N-undecylenoyl glycine:benzoic acid:sodium dehydroacetate in the ratio of 1:1:1:1 by weight.

In another embodiment, the present invention provides the advantage of cold-processability of the composite blend of the preservative composition.

In addition to free of dust explosion hazard, ease of incorporation is the additional biggest advantage of the present invention. Typically, incorporation of solid antimicrobial is always a problem if it does not dissolve in water readily or in some other personal care ingredients. The incorporation of antimicrobial blend of the present invention in personal and home care formulations is extremely facile due to its low melting point (around 60° C.) which makes it easy to incorporate if the personal care formulation involves mixing of ingredients at elevated temperatures. The composite blend of the present invention is soluble in glycolic or alcoholic personal care ingredients such as propylene glycol, 2-ethylhexylglycerin, caprylyl glycol etc. Some of these liquid personal ingredients can be used to pre-dissolve the antimicrobial blend of this composition and then introduced to the rest of the formulation that is being stirred at room temperature or at elevated temperature. The properties of being low melting and of being soluble in common personal care ingredients offer a lot of ease-of-incorporation while formulating variety of personal care formulations. If the processing of the personal care or home care formulation does not involve heating at all then the blend of Example 2 is simply incorporated by a) stirring it with part of water for few minutes to form aqueous dispersion and b) adding all other ingredients (including surfactants) of the home care/personal care composition to this fine dispersion of antimicrobial blend and mixing is continued at room temperature to get the homogeneous mass (FIGS. 1a, 1b & 1c)).

Figure 2:
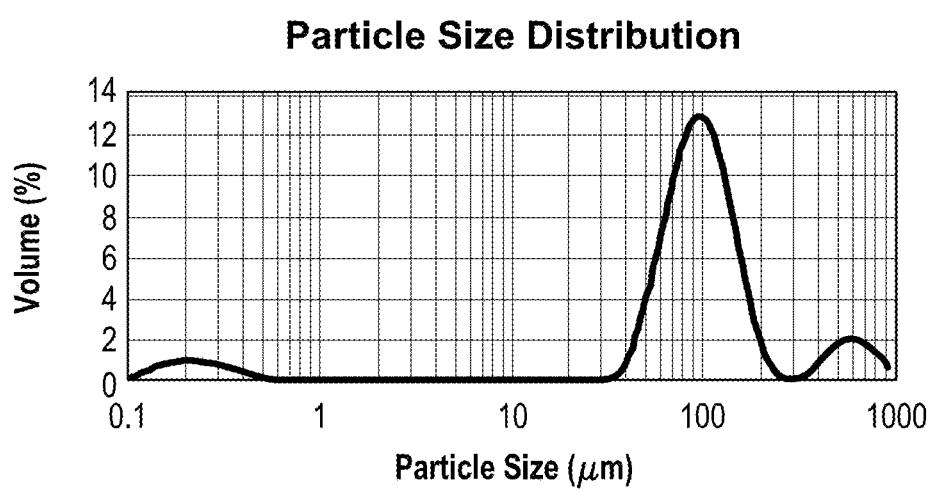
FIG. 2 shows particle size analysis of the aqueous dispersion showed that d(0.5) is 97µ and d(0.9) is 214µ.

FIG. 1a shows the typical flake form of the composition of the present invention prepared in accordance with example 2, whereas FIG. 1b shows the aqueous fine dispersion of 1% at room temperature and FIG. 1c depicts clear solution of this dispersed antimicrobials at room temperature in the presence of 8 to 12% surfactant mix, typically anionic or amphoteric surfactants. This 8 to 12% surfactant mix is the usual range that can be used for home and personal care products. This ease of dispersion of the anti-microbial blend of the present invention in water and subsequent solubility of the same in the presence of surfactants is very surprising. The particle size analysis of the aqueous dispersion showed that d(0.5) is 97μ and d(0.9) is 214μ (FIG. 2). This aqueous suspension behavior is explained by the experiments enlisted in Table II.

The data given in Table II is generated on 300 g scale experiments by dispersing 1% of antimicrobial preservative compositions in water & solubilizing the dispersed particles in the mixture of 10% sodium laureth sulphate and 2% cocamidopropyl betaine at the 300 rpm. The addition of individual ingredients (N-capryloyl glycine (CG), N-undecylenoyl glycine (UG), benzoic acid (BA) and sodium dehydroacetate (SDA) in 1:1:1:1 ratio by weight) to stirred water so as to get about 1% concentration at room temperature does not result in a dispersion (Table II, entry 1). Similarly, it should also be noted that the blend of four acids, namely, N-capryloyl glycine, N-undecylenoyl glycine, benzoic acid and dehydroacetic acid (DA) in the ratio of 1:1:1:1 by weight, does not get dispersed in water at any temperature (Table II, entry 2). In both cases upon addition of surfactants (sodium laureth sulphate 10% and cocamido propyl betaine 2%) and continued stirring of 3 h is needed for complete dissolution of the blend. However, the composite blend of the present invention in its flake form gets dispersed in water and its further dissolution in surfactant dispersion in water. Partial use of sodium salt of dehydroacetic acid along with partial amount of dehydroacetic acid (Table II, entry 5) results in losing the degree of ease of dispersion that is normally exhibited by the blend of present invention.

Needless to say that with the facility of high speed, high shear mixing (Silverson type or any other rotor-stator type; http://www.silverson.com/us/products/laboratory•mixers/) the dispersion time in water as well as solution time in the presence of surfactants are further reduced.

But the order of relative ease of dispersion remains the same. For example, 1% dispersion (4 g of composition of Example 2 in 400 mL water) and dissolution (in the presence of 10% surfactants) with Silverson L5M-A mixer with Square hole high shear screen (at 3000 rpm and 25° C.) is accomplished in three minutes whereas the individual ingredients took about 10 min for creation of homogeneous dispersion and finally solution on the same scale. However, most of the industry uses cold process (without any heating) and simple mixing (and not high shear homogenizer) for personal care formulations like shampoos or hand-dish washes where batch size is usually 10 to 50 MT. It is uneconomical to heat such huge reaction mass and hence ease of cold dispersibility of solid ingredients does matter a lot in these industries.

TABLE II

| | The composition of anti-microbial blend | Acid value | Melting point | Time taken for dispersion of 1% anti-microbial blend in water (300 rpm, rt.) | Time taken for dissolution of 1% anti-microbial blend in water in the presence of surfactants (300 rpm) 10% SLES and 2% CAPB, at rt. |
|---|---|---|---|---|---|
| 1 | All four ingredient in isolated form UG, CG, BA and SDA | — | — | Does not disperse | 3 h |
| 2 | All four in acid form (1:1:1:1) as one blend | 315 | 52-60° C. | Does not disperse | 3 h |
| 3 | UG/CG/DA and sodium benzoate (1:1:1:1) | Does not form a homogeneous blend | — | — | — |
| 4 | UG/CG/BA and SDA (1:1:1:1) (Example 2) | 240 | 55-65° C. | Complete dispersion in 3 h | Complete dissolution in 1 h |
| 5 | UG/CG/BA and SDA (1:1:1.5:0.5) | 292 | 58-68° C. | Does not disperse | 3 h | solutions at room temperature is very facile (1 h) (Table II, entry 4). It requires only ⅓$^{rd}$ of the time to dissolve in surfactant solution compared to the blend of 'all four-acids' (entry 2).

It is pertinent to mention here that the blend of N-capryloyl glycine, N-undecylenoyl glycine, dehydroacetic acid and sodium benzoate is inhomogeneous and does not show facile dispersion in water or dissolution in surfactants (Table II, entry 3), when compared to the composite blend of the present invention (Table II, entry 4). Also, it has been found that the blend of the present invention requires the entire quantity of dehydroacetic acid in its sodium salt for facile Cold processability of the preservative composition of the present invention is illustrated in Example 6. The pre-dispersed blend of Example 2 in water, is readily dissolved by anionic surfactants as demonstrated in Examples 5, 6 & 7. Example 5 illustrates cold processing of a hand dish wash that is preserved with antimicrobial composition of Example 2. In this example the dispersion of antimicrobial composition in water is made first and to this dispersion the other ingredients like lauryl ether sulphate, alkyl amine oxide and alkyl polyglucoside are added at room temperature. Example 6 illustrates the shampoo formulation effected at room temperature. To the dispersion of antimicrobial of the present invention in water, other ingredients like anionic surfactant and the amphoteric surfactant are added at room temperature. To this Galaxy Sparkle 660 (a pearlizer consisting of an alkanol amide and the pearly wax, Ethylene glycol distearate) is added and the whole is mixed at room temperature to get pearly shampoo. Such cold pearlizer compositions are available from several other manufactures like BASF (Euperlan), Lubrizol (QuickPearl) and Solvay (Mirasheen). In case of emulsion type formulation (Example 7), to an aqueous dispersion of the antimicrobials of the present invention, surfactants or other oily ingredients are added at room temperature and the whole mass is homogenized using Silverson type homogenizer till a uniform product is obtained. Thus, the preservative blend of the present invention exhibits equal ease of incorporation in aqueous surfactant based formulations (shampoo/shower gels type) as well as emulsion type cream formulations. Pre-dispersion of the anti-microbial composition of this patent application in water allows its incorporation to both 'rinse-off' or 'leave-on' type of formulations at room temperature.

In another embodiment, the invention demonstrates antimicrobial efficacy of the antimicrobial blend of the present invention.

The minimum inhibitory concentration (MIC) against bacteria, yeast and mold is given in Table III. It is to be noted that MIC numbers for the present antibacterial composite blend against all organisms is less than 0.5%. (Table III) The Minimum Inhibitory Concentration of Composition of Example 2 (Table III)

TABLE III

| Microorganism | MIC of Example 2 (% active) |
| --- | --- |
| Staphylococcus aureus ATCC 6538 | 0.4 |
| Pseudomonas aeruginosa ATCC 15442 | 0.4 |
| Escherichia coli ATCC 8739 | 0.4 |
| Candida albicans ATCC 10231 | 0.3 |
| Aspergillus niger ATCC 16404 | 0.4 |
| Propiniobacterium acnes MTCC 1951 | 0.3 |
| Malassezia furfur MTCC 1374 | 0.3 |

The preservation efficacy of composition of Example 2 was tested by incorporating it in two types of personal care formulations that have significant quantity of water, namely, a shampoo (rinse-off application, Example 3) and an oil-in-water cream formulation (leave-on application, Example 4) at about 1.0% active level. Both formulations were then challenged by inoculating various microbes as per the standard protocol of CTFA ('Evaluation of preservatives to protect cosmetics' by D. Orth in *Cosmetics and Toiletries*, March 91). The initial inoculation level of microbes for this study was around $10^6$ to $10^7$ cfu/ml for bacteria and $10^5$ for yeast and mold in the formulation. Both 'rinse-off' and 'leave-on' formulations passed the challenge tests and the results are tabulated in Tables IV and Table V. Aqueous formulations like shampoo with pH of 6.0 can be easily preserved with 0.5 to 0.75% of composition of the present invention. Similarly, emulsion type formulations can be preserved with 0.5% level of antimicrobial composition of the present invention. The antimicrobial composition of the present invention can be used for any personal care or home care formulation with or without significant amount of water in it. Examples of personal care formulation without water would be face powder or face wash. The solid nature of this present invention makes it amenable to solid personal care and home care products that are either free flowing powders or compact solids. Example 8 illustrates the solid composition of effervescent powder face cleanser.

TABLE IV

Challenge test as per PCPC: Shampoo (pH 6.0) with 1.0% composition of Example 2

| Test Organisms | 0 h | 48 Hours | 7 Days | 14 Days | 21 days | 28 Days |
| --- | --- | --- | --- | --- | --- | --- |
| Staphylococcus aureus | $3.8 \times 10^6$ | <10 | <10 | <10 | <10 | <10 |
| Escherichia coli | $5.8 \times 10^6$ | <10 | <10 | <10 | <10 | <10 |
| Propionibacterium acnes | $4.0 \times 10^6$ | <10 | <10 | <10 | <10 | <10 |
| Pseudomonas aeruginosa | $2.8 \times 10^6$ | <10 | <10 | <10 | <10 | <10 |
| Candida albicans | $3.8 \times 10^6$ | <10 | <10 | <10 | <10 | <10 |
| Aspergillus niger | $5.7 \times 10^6$ | <10 | <10 | <10 | <10 | <10 |
| Malassezia furfur | $5.6 \times 10^6$ | <10 | <10 | <10 | <10 | <10 |

TABLE V

Challenge test as per CTFA: Cream (emulsion) at pH 6.0 with 1.0% composition of Example 2

| Test Organisms | 0 hr | 48 Hours | 7 Days | 14 days | 21 days | 28 Days |
| --- | --- | --- | --- | --- | --- | --- |
| Staphylococcus aureus | $5.6 \times 10^6$ | <10 | <10 | <10 | <10 | <10 |
| Escherichia coli | $3.3 \times 10^6$ | <10 | <10 | <10 | <10 | <10 |
| Propionibacterium acnes | $5.6 \times 10^6$ | $5.2 \times 10^2$ | <10 | <10 | <10 | <10 |
| Pseudomonas aeruginosa | $1.3 \times 10^6$ | $2.2 \times 10^1$ | <10 | <10 | <10 | <10 |
| Candida albicans | $4.9 \times 10^6$ | <10 | <10 | <10 | <10 | <10 |
| Aspergillus niger | $8.2 \times 10^6$ | <10 | <10 | <10 | <10 | <10 |
| Malassezia furfur | $9.8 \times 10^6$ | <10 | <10 | <10 | <10 | <10 |

EXAMPLES

The present invention is now described by way of working and non limiting illustrative examples. The details of the invention provided in the following examples is given by the way of illustration only and should not be construed to limit the scope of the present invention.

Benzoic acid and sodium dehydroacetate were purchased from Ganesh Benzoplast, India and FenChem Group, China respectively. Caprylic acid and undecylenic acid were purchased form VVF Ltd, Mumbai, India. Milcoside was procured from LG, S. Korea. Rest of the ingredients were supplied by Galaxy Surfactants Ltd, India.

Example 1: Synthesis of Blend of N-Undecylenoyl Glycine and N-Capryloyl Glycine (1:1 by Weight)

To a stirred mixture of glycine (225 g, 3.0 gmol) in water (1700 g) at 25° C. under nitrogen, was added mixture of capryloyl chloride (255 g, 1.54 gmol) and undecylenoyl chloride (255 g, 1.24 gmol) and sodium hydroxide solution (478 g of 48.5% aqueous solution, 5.8 mmol) simultaneously while maintaining temperature between 20 to 25° C. and pH between 9.5 to 10.5. The addition takes 4 to 5 hours depending on the efficiency of temperature control. The reaction mass was stirred for additional two hours. It was further acidified by addition of concentrated hydrochloric acid. The precipitated solid was filtered and washed with plenty of water to remove the mineral acidity. The mixture of lipidated glycines was obtained as solid powder (595 g, 95%) after vacuum drying at 65° C. The dried powder had moisture less than 1% and acid value of 258. The HPLC analysis of powder indicated it to nearly 50:50 ratio of N-undecylenoyl glycine and N-capryloyl glycine. The mixture of two lipidated glycines melts at 85 to 90° C.

Example 2: Preparation of Flakes of Composite Blend of N-Undecylenoyl Glycine, N-Capryloyl Glycine, Benzoic Acid and Sodium Dehydroacetate in the Ratio of 1:1:1:1 by Weight A mixture of N-undecylenoyl glycine, N-capryloyl glycine (500 g) from Example 1, under nitrogen was heated to 85-90° C. To the molten transparent mass, benzoic acid (250 g) and sodium dehydroacetate (250 g) were added and continued to stir for half an hour till the reaction mass became transparent. The reaction mass was converted into flakes by pouring over a cooled surface ensuring the thickness of flakes is 2 to 4 mm. The analysis of the flakes of the above composition is given in table below.

| | |
|---|---|
| Appearance/Nature | Off-white Flakes |
| Odour | Characteristic |
| pH (1% aqueous dispersion) | 3.5 |
| Acid Value, mg KOH/g | 240 |
| Moisture Content, % by mass | <1% |
| Melting point (in ° C.) | 55-65 |

Example 3: Preparation of Shampoo and its Preservation with the Composite Blend of Example 2

| Components | Trade Name | (% W/W) |
|---|---|---|
| Phase A | | |
| Water (Aqua) | DM Water | 70.00 |
| Sodium laureth sulphate (70%, 2 EO) | Galaxy LES 70 | 20.00 |
| Phase B | | |
| Cocomonoethanol amide | Galaxy 100 | 3.00 |
| Ethylene glycol distearate | Galaxy 610 | 2.00 |
| Phase C | | |
| Preservative | Composition of Example 2 | 1.0 |
| Caustic Lye, 48% | | q.s. to pH 6 to 6.5 |
| Fragrance, Color | | q.s |

Procedure:

All the ingredients of phase A were heated to 75° C. under slow stirring. To this stirred Phase A, Phase B was added and mixed until homogeneous. The reaction mix was then cooled down to room temperature and phase C was added, and stirred until uniform consistency. pH of the final formulation was adjusted with 48% Caustic Lye and the fragrance and color were added and blended together.

Example 4: Preparation O/W Cream and its Preservation with the Composite Blend of Example 2

| Components | Trade Name | (% W/W) |
|---|---|---|
| Phase A | | |
| Water (Aqua) | DM Water | 70.00 |
| Glycerin | Glycerin | 2.00 |
| Phase B | | |
| Paraffinum Liquidum | Mineral oil | 15.00 |
| Stearic Acid | Stearic Acid | 2.00 |
| Glyceryl Stearate | Glyceryl Stearate | 5.00 |
| Cetearyl Alcohol | Cetearyl Alcohol | 3.50 |
| Phase C | | |
| Preservative | Composition of Example 2 | 0.80 |
| Fragrance, Color | | q.s |

Procedure:

Heated the contents of Phase A and Phase B separately up to 75° C. with stirring. Added phase B to phase A with constant stirring. Homogenized for 2 minutes, continued stirring for 15 minutes. Added phase C. Mixed well Cooled the mass while mixing. Added fragrance and color when the mix is at room temperature and blended.

Example 5: Cold Process for Hand Dish-Wash and its Preservation with the Composite Blend of Example 2

| Components | Trade Name | (% W/W) |
|---|---|---|
| Phase A | | |
| Water (Aqua) | DM Water | 47.0 |
| Sodium laureth sulphate (70%, 2 EO) | Galaxy LES 70 | 21.5 |
| Lauryl Amine Oxide, (30%) | Galaxy LAO | 6.0 |
| Lauryl Glucoside (50%) | Milcoside 200 | 4.0 |
| Disodium EDTA | | 0.3 |
| Phase B | | |
| Sodium Chloride | | 1.0 |
| Citric Acid | | 0.2 |
| Preservative | Composition of Ex 2 | 1.0 |
| Water | | 20.0 |
| Fragrance, Color | | q.s |

Procedure:

Composition of Example 2 in Phase B was charged to the reactor with mentioned amount of water in Phase B and stirred for 15 min to get a fine dispersion of it. To this Phase A ingredients were added in the sequence and stirred at room temperature till a homogeneous mass is obtained (2 h). Sodium Chloride was added to the above mass and mixed. To this reaction mixture, color and fragrance were added to get the hand-dish wash. pH of the final formulation was adjusted to 5.5 with 50% citric acid.

Example 6: Cold Process for Shampoo and its Preservation with the Composite Blend of Example 2

| Components | Trade Name | (% W/W) |
|---|---|---|
| Phase A | | |
| Sodium laureth sulphate (70%, 2 EO) | Galaxy LES 70 | 10.0 |
| Cocoamidopropyl betaine | Galaxy CAPB | 2.0 |
| Phase B | | |
| Sodium Laureth Sulfate, Ethylene glycol Distearate Cocamide MEA | Galaxy Sparkle 660 | 10.0 |

| Components | Trade Name | (% W/W) |
|---|---|---|
| Phase C | | |
| Preservative | Composition of Example 2 | 1.0 |
| Water (Aqua) | DM Water | 67.0 |

Procedure:

Phase C was charged to the reactor and stirred for 15 min to get a fine dispersion of preservative blend of Example 2. To this stirred Phase C, ingredients of Phase A were added sequentially and stirring was continued at room temperature. To the stirred mass cold pearlizer mix of Phase B was added and stirring was continued till a homogeneous mass is obtained (2 h). To this reaction mixture, color and fragrance were added to get the final shampoo. The pH of the final formulation was 6.0

Example 7: Cold Process of a O/W Cream and its Preservation with the Composite Blend of Example 2

| Components | Trade Name | (% W/W) |
|---|---|---|
| Phase A | | |
| Isopropyl Palmitate | | 9.5 |
| Olive Oil | | 1.0 |
| Vitamin E | | 0.1 |
| Ethylhexyl methoxycinnamate | Galaxy OMC (HP) | 0.5 |
| Phase B | | |
| Hydroxyethyl cellulose | Natrosol 250 HHR | 1.0 |
| Glycerin | | 5.0 |
| Laureth-7 | Galaxy MW 257 | 5.0 |
| Water | | 86.9 |
| Preservative | Composition of Example 2 | 1.0 |
| Phase C | | |
| Caustic Lye, 48% | | 0.2 |
| Fragrance | | q.s |

Procedure:

Composition of Example 2 was dispersed in water under stirring for 15 min. Hydroxyethyl cellulose was added to the above dispersion slowly under stirring so that it swells uniformly in water. The remaining ingredients of Phase B were added to the above mass sequentially and mixed. Phase A ingredients were separately charge in another vessel and mixed at RT to form a homogeneous blend. Blend prepared with phase A ingredients was then added to Phase B mixture and homogenized for 5 min until a emulsion is obtained. Fragrance was added to the cream and pH of cream was adjusted to 6.0 with 48% caustic lye solution.

Example 8: Preservation of Effervescent Powder Face Wash with the Composite Blend of Example 2

| Components | Trade Name | (% W/W) |
|---|---|---|
| Phase A | | |
| Sodium Bicarbonate | | 33.8 |
| Fumed Silica | AEROSIL R-972 | 1.0 |
| Phase B | | |
| Citric Acid | | 25.2 |
| Preservative | Composition of Ex 2 | 1.0 |
| Sodium Lauryl Sulfate | Galaxy LES (P) | 19 |
| Phase C | | |
| Sodium Lauroyl Sarcosinate | Galsoft NaLS (P) | 20 |
| Fragrance | | q.s |

Procedure:

Ingredients of Phase A were mixed and then ingredients of Part B were added to Part A sequentially and mixed well. Part C ingredients were then added to above mixture and mixed well. The dry powder mixer was further pulverized to remove any gritty feel of powder. The pH of 5% solution of above formulation was 6.0.

Advantages of the Invention

1) The preservative composition of the present patent application avoids all toxic antimicrobials like parabens, halogenated chemicals, phenolic and alcoholic chemicals and formaldehyde releasers. The preservative composition of the present patent application is based on two lipidated glycines, namely, N-capryloyl glycine and N-undecylenoyl glycine and two organic acids, namely, benzoic acid and dehydroacetic acid in its sodium salt form. All ingredients are well accepted by the personal care industry, with proven benefits. All four ingredients of this composition are non-toxic to human. No adverse toxicity findings are reported in the literature so far.

2) The preservative composition of this patent application protects the personal care formulations from bacteria as well as from fungi. The combination of four antimicrobials with distinctly different structural features (straight chain aliphatic, cyclic aliphatic, aromatic, conjugated unsaturation, isolated unsaturation) would result in different mechanisms of attacking microbes that come with a variety of structural differences in the cell envelopes (glycocalyx, outer membrane and cytoplasmic membrane of non-nucleated Gram-ve and Gram-ve bacteria and nucleated fungi). Four pronged combinatory attack on a variety of microbes offered by the composition of the patent application lowers the dosage of individual ingredient significantly. The four pronged combinatory attack would also prevent the microbes from acquiring the resistance towards preservative composition. Use of several antimicrobials for preservation is a well-established defense strategy for restricting microbes from adapting and mutating to resistant forms.

3) The solid flake form of preservative composition of this patent application avoids any health hazard that might arise due to dusting of fine powder. The flake form also avoids the dust explosion fire hazard that is associated with fine dust of materials with lower MIEs (Minimum Ignition Energy). The composition can also be made in any other solid forms such as granules, cubes etc.

4) The preservative composition of the present invention in solid flake form is easy to incorporate. It gets quickly dispersed in water at room temperature and hence easily amenable to personal care formulations that are manufactured by cold processing.

5) The solid easy-to-use preservative composition of the present patent application is compatible with all cosmetic ingredients, stable towards any oxidizing or reducing agents and within the normal range of pH (4.0 to 7.0) of personal care formulations.

6) The preservative composition of the present invention is suitable for dry forms of home and personal care products like powder face wash or compacts with negligible amount of water.

Anyone with the reasonable level of knowledge of in the art would understand that the solid, easy-to-use, broad spectrum preservative composition of the present invention can be used with additional anti-microbial compounds or adjuvants that can enhance or boost antimicrobial activity synergistically. The examples of such adjuvants are ethylhexyl glyceryl ether, caprylyl glycol, 1,3-Propane diol or EDTA etc.

The invention claimed is:

1. A cold-processable antimicrobial composition in non-dusting composite blend form, comprising a) N-capryloyl glycine, b) N-undecylenoyl glycine, c) benzoic acid, and d) sodium dehydroacetate; wherein
   a. benzoic acid and sodium dehydroacetate are used in a 1:1 ratio by weight; and
   b. the cold-processable antimicrobial composition does not include phenoxyethanol.

2. The cold-processable antimicrobial composition of claim 1, wherein the cold-processable antimicrobial composition is free of surfactants.

3. A process for preparation of a cold-processable homogeneous antimicrobial composition in non-dusting composite blend form which is free of surfactants, comprising N-capryloyl glycine, N-undecylenoyl glycine, benzoic acid, and sodium dehydroacetate in a ratio of 1:1:1:1 by weight, comprising:

a) Melting a blend of N-Capryloyl glycine and N-undecylenoyl glycine in 1:1 ratio by weight to obtain molten mass;
   b) Adding benzoic acid and sodium dehydroacetate in 1:1 ratio by weight to the molten mass under stirring at about 75° C. till the reaction mass becomes clear; and
   c) Cooling the blend to obtain preservative composition in the form of non-dusting composite blend.

4. The process according to claim 3, wherein the non-dusting solid form may be selected from the group consisting of cubes, flakes, granules, powder, a compact, and combinations thereof.

5. A personal care composition comprising the antimicrobial composition of claim 1 in an amount of 0.3 to 2% of the personal care composition.

6. The personal care composition according to claim 5, wherein the personal care composition is selected from the group consisting of a powder, granules, a compact, a lotion, a cream, a solution, a body-washes, sera, a hand wash, an intimate hygiene wash, a wipe, an emulsion, and combinations thereof.

7. A home care composition comprising the antimicrobial composition of claim 1 in an amount of 0.3 to 2% of the home care composition.

8. The home care composition according to claim 7, wherein the home care composition is selected from the group consisting of a powder, granules, a lotion, a cream, a solution, a wipe, an emulsion, a dish washing formulation, a surface cleanser, and combinations thereof.

9. The cold-processable antimicrobial composition of claim 1, wherein N-capryloyl glycine, N-undecylenoyl glycine, benzoic acid, and sodium dehydroacetate are used in a 1:1:1:1 ratio by weight.

* * * * *